United States Patent
Seligson et al.

(10) Patent No.: US 10,139,528 B1
(45) Date of Patent: Nov. 27, 2018

(54) COMPOUND OBJECTIVES FOR IMAGING AND SCATTEROMETRY OVERLAY

(71) Applicant: KLA-Tencor Corporation, Milpitas, CA (US)

(72) Inventors: Joel Seligson, D.N. Misgav (IL); Vladimir Levinski, Migdal HaEmek (IL); Yuri Paskover, Caesarea (IL); Amnon Manassen, Haifa (IL); Daniel Kandel, Aseret (IL); Andrew V. Hill, Portland, OR (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/408,351

(22) Filed: Jan. 17, 2017

Related U.S. Application Data

(60) Provisional application No. 62/280,708, filed on Jan. 20, 2016.

(51) Int. Cl.
| | |
|---|---|
| *G02B 3/08* | (2006.01) |
| *G01N 21/47* | (2006.01) |
| *G01N 21/17* | (2006.01) |

(52) U.S. Cl.
CPC ........... *G02B 3/08* (2013.01); *G01N 21/4795* (2013.01); *G01N 2021/1734* (2013.01)

(58) Field of Classification Search
None
See application file for complete search history.

(56) References Cited

U.S. PATENT DOCUMENTS

| | | | | |
|---|---|---|---|---|
| 6,330,118 B1* | 12/2001 | Daschner | ............. | G02B 5/1876 359/565 |
| 7,158,468 B2* | 1/2007 | Takeuchi | ............. | G02B 5/1895 369/112.04 |
| 7,664,003 B2* | 2/2010 | Ogiwara | ............. | G11B 7/1353 369/112.23 |
| 8,441,639 B2* | 5/2013 | Kandel | ................ | G01N 21/956 356/369 |
| 2003/0156276 A1* | 8/2003 | Bowes | .................... | G01B 11/26 356/124 |
| 2004/0208111 A1* | 10/2004 | Hayashi | ............... | G11B 7/1353 369/112.26 |
| 2008/0080357 A1* | 4/2008 | Tanaka | ................. | G11B 7/1353 369/112.23 |
| 2013/0265576 A1* | 10/2013 | Acher | ....................... | G01J 4/00 356/369 |
| 2015/0036142 A1* | 2/2015 | Kandel | ................ | G01N 21/956 356/445 |
| 2015/0377794 A1* | 12/2015 | Nesbitt | ............. | G01N 21/8806 356/369 |

(Continued)

*Primary Examiner* — Shawn Decenzo
(74) *Attorney, Agent, or Firm* — Hodgson Russ LLP

(57) ABSTRACT

Objective lenses and corresponding optical systems and metrology tools, as well as methods are provided. Objective lenses comprise a central region conforming to specified imaging requirements and a peripheral region conforming to specified scatterometry requirements. The optical systems may comprise common-path optical elements configured to handle both imaging and scatterometry signals received through the objective lens. Using a single objective lens simplifies the design of the optical system while maintaining, simultaneously, the performance requirements for imaging as well as for scatterometry.

15 Claims, 2 Drawing Sheets

(56) References Cited

U.S. PATENT DOCUMENTS

2016/0047744 A1\* 2/2016 Adel .................. G03F 7/70633
356/401
2017/0336198 A1\* 11/2017 Adel .................... G01B 11/272

\* cited by examiner

COMPOUND OBJECTIVES FOR IMAGING AND SCATTEROMETRY OVERLAY

CROSS REFERENCE TO RELATED APPLICATIONS

This application claims the benefit of U.S. Provisional Patent Application No. 62/280,708 filed on Jan. 20, 2016, which is incorporated herein by reference in its entirety.

BACKGROUND OF THE INVENTION

1. Technical Field

The present invention relates to the field of metrology, and more particularly, to an objective in an optical system of a metrology tool.

2. Discussion of Related Art

Metrology methods include measuring overlays between target layers, using e.g., imaging targets, from which an image of the target at the field plane is derived and analyzed and/or scatterometry targets, from which diffraction signals at the pupil (Fourier) plane are derived and analyzed.

SUMMARY OF THE INVENTION

The following is a simplified summary providing an initial understanding of the invention. The summary does not necessarily identify key elements nor limits the scope of the invention, but merely serves as an introduction to the following description.

One aspect of the present invention provides an objective lens in an optical system of a metrology tool, the objective lens comprising a central region conforming to specified imaging requirements and a peripheral region conforming to specified scatterometry requirements.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Figure 1:
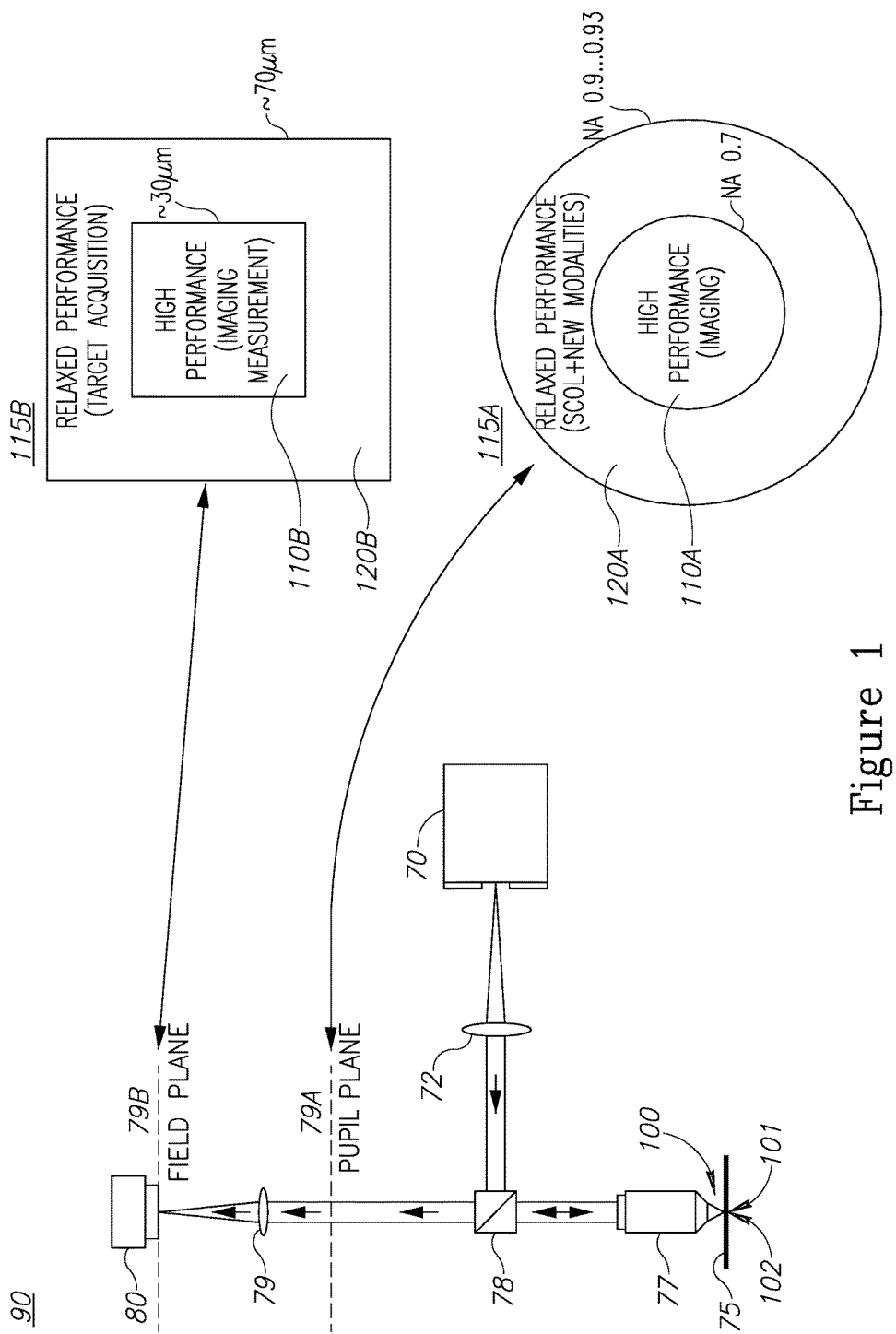
FIG. 1 is a high level schematic illustration of an optical system of a metrology tool and suggested objective lenses, defined by requirements, according to some embodiments of the invention.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Objective lenses and corresponding optical systems and metrology tools, as well as methods are provided. Objective lenses comprise a central region conforming to specified imaging requirements and a peripheral region conforming to specified scatterometry requirements. The optical systems may comprise common-path optical elements configured to handle both imaging and scatterometry signals received through the objective lens. Using a single objective lens simplifies the design of the optical system while maintaining, simultaneously, the performance requirements for imaging as well as for scatterometry.

Compound objectives are provided, which combine, in one objective lens, the high performance requirements of imaging overlay at a medium NA (Numerical Aperture), and the relaxed performance requirements of scatterometry overlay at a high NA. The objectives also enable additional, novel metrology modalities to be performed.

The disclosed objective lenses improve over current overlay metrology systems which combine on one platform both an imaging overlay metrology optical head and a scatterometry overlay metrology optical head in order to satisfy high-end customer requirements. The need for two separate heads stems largely from the fact that the optical specifications for the objective lenses are quite different. For example, imaging overlay objective typically has an NA of 0.7 and imposes very stringent requirements for the optical performance, especially concerning the on-axis and off-axis asymmetrical aberrations. On the other hand, scatterometry overlay objectives typically have a NA of 0.9 with much less demanding aberration requirements than those for imaging overlay. The requirement for two separate heads causes the metrology tool to be large in size in order to provide the physical space for the two heads (objectives and associated optical components) as well as access to the two heads for adjustments and service. Disclosed objective lenses remove the requirement for two separate optical heads and thus enable more compact metrology tools.

FIG. 1 is a high level schematic illustration of an optical system 90 of a metrology tool and suggested objective lenses 100, defined by requirements 115A and/or 115B, according to some embodiments of the invention. Optical system 90 comprises, schematically, light source(s) 70, optical element(s) 72, beam splitter(s) 78 directing the incoming illumination through a single optics head 77 with objective lens 100 onto at least one imaging target 101 and/or at least one scatterometry target 102 on a wafer 75, beam splitter 78 directing reflected and/or refracted radiation via optical element(s) 79 to detector(s) 80. A field plane 79B is indicated schematically at the plane at which the target image converges and a pupil plane 79A is indicated schematically at the Fourier plane at which the signal from the target is collimated. Detector(s) 80 may be set at either or both field and image planes 79B, 79A respectively.

Requirements 115A, 115B that define objective lens 100 are indicated alternatively or complementarily with respect to pupil and field planes 79A, 79B, respectively. Central regions 110A, 110B are defined to provide high performance required for imaging while peripheral regions 120A, 120B are defined to provide relaxed performance sufficient for any of: target acquisition, scatterometry and/or other measurement modalities.

Objective lenses 100 in optical system 90 of the metrology tool may comprise a central region (110A, 110B) conforming to specified imaging requirements and a peripheral region (120A, 120B) conforming to specified scatterometry requirements. Common-path optical elements may be configured to handle both imaging and scatterometry signals received through objective lens 100, thus simplifying optical system 90. Optical systems 90 and corresponding metrology tools are considered part of the present invention.

For example, central region 110A may comprise about 0.7 NA while peripheral region 120A may comprise 0.7 to 0.9 or 0.93 NA at pupil plane 79A, and/or central region 110B may be about 30 μm wide while peripheral region 120B may be about 70 μm wide at field plane 79B.

Figure 2:
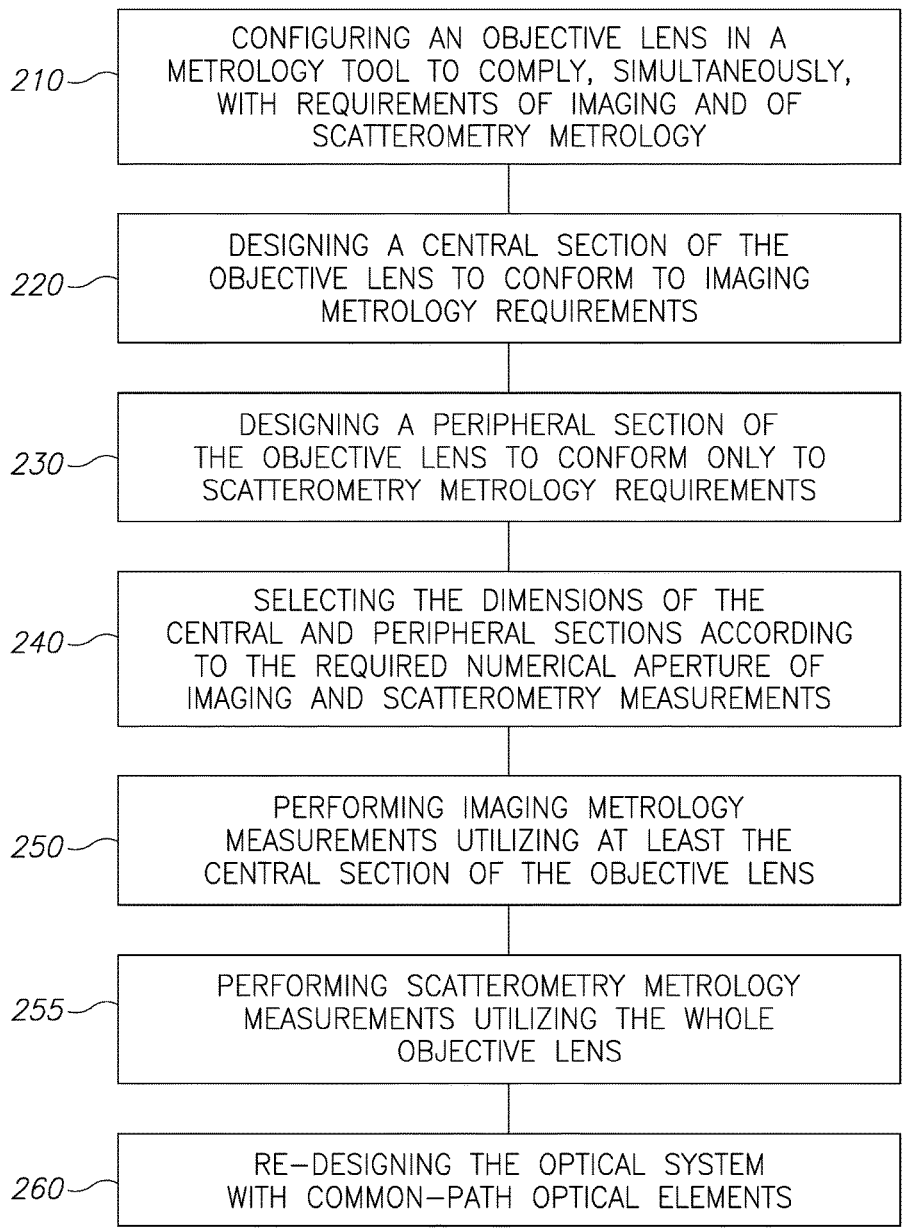
FIG. 2 is a high level flowchart illustrating a method, according to some embodiments of the invention.

FIG. 2 is a high level flowchart illustrating a method 200, according to some embodiments of the invention. Method 200 may comprise configuring an objective lens in an optical system of a metrology tool to comply, simultaneously, with requirements of imaging and of scatterometry metrology (stage 210). Method 200 may comprise designing a central section of the objective lens to conform to imaging metrology requirements (stage 220) and designing a peripheral section of the objective lens to conform only to scatterometry metrology requirements (stage 230). Method 200 may comprise selecting the dimensions of the central and peripheral sections according to the required numerical aperture of imaging and scatterometry measurement (stage 240).

Method 200 may further comprise performing imaging metrology measurements utilizing at least the central section of the objective lens (stage 250) and performing scatterometry metrology measurements utilizing the whole objective lens (stage 255).

Method 200 may further comprise re-designing the optical system of the metrology tool with common-path optical elements (stage 260) to simplify the system's design.

Disclosed objective lenses 100 combine in an economical way the requirements for both imaging overlay objectives and scatterometry overlay objectives, to simplify optical system 90 of the metrology tool while maintaining its level of performance. In particular, disclosed objective lenses 100 avoid designing the whole objective lens (e.g., 0.9 NA) to provide the stringent requirements of imaging metrology in order to reduce production cost and complexity. Disclosed objective lenses 100 thus enable the construction of a simpler, smaller, and less costly optical metrology head. A common optical path, both for illumination and collection, could be kept where feasible, with a split to different modalities done only where necessarily needed. From the cost point of view, it is expected that not only compound objective lens 100 would cost less than the two currently used (imaging and scatterometry) objectives combined, but that additional cost savings may be realized as well from using common-path optical components instead of two sets of optics, as well as from handling and maintaining a smaller and lighter optical head.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. An objective lens in an optical system of a metrology tool, the objective lens comprising a central region configured for imaging and a peripheral region configured for scatterometry, wherein the central region has a numerical aperture of 0.7 NA and the peripheral region has a numerical aperture of greater than 0.7 NA to 0.93 NA.

2. The objective lens of claim 1, wherein the objective lens is positioned in a pupil plane of the optical system.

3. The objective lens of claim 1, wherein the central and peripheral regions have widths of 30 μm and 70 μm respectively, and wherein the objective lens is positioned in a field plane.

4. An optical system in a metrology tool comprising the objective lens of claim 1.

5. The optical system of claim 4, further comprising common-path optical elements configured to handle both imaging and scatterometry signals received through the objective lens.

6. A metrology tool comprising the optical system of claim 5.

7. The objective lens of claim 1, wherein the numerical aperture of the peripheral region is greater than 0.7 NA to 0.9 NA.

8. The objective lens of claim 7, wherein the numerical aperture of the peripheral region is 0.9 NA.

9. A method comprising configuring an objective lens in an optical system of a metrology tool to comply, simultaneously, with requirements of imaging and of scatterometry metrology, by designing a central section of the objective lens configured for imaging metrology and designing a peripheral section of the objective lens configured for scatterometry metrology, wherein the central region has a numerical aperture of 0.7 NA and the peripheral region has a numerical aperture of greater than 0.7 NA to 0.93 NA.

10. The method of claim 9, further comprising selecting dimensions of the central and peripheral sections according to the required numerical aperture of imaging and scatterometry measurement.

11. The method of claim 9, further comprising performing imaging metrology measurements utilizing at least the central section of the objective lens and performing scatterometry metrology measurements utilizing the whole objective lens.

12. The method of claim 9, further comprising re-designing the optical system of the metrology tool with common-path optical elements.

13. The method of claim 9, wherein the numerical aperture of the peripheral region is greater than 0.7 NA to 0.9 NA.

14. The method of claim 13, wherein the numerical aperture of the peripheral region is 0.9 NA.

15. The method of claim 9, wherein the objective lens is positioned in a pupil plane of the optical system.

\* \* \* \* \*